United States Patent [19]

Cohen et al.

[11] 4,150,138

[45] Apr. 17, 1979

[54] METHOD OF REDUCING BLOOD PRESSURE WITH THIOUREA DERIVATIVES AND GUANIDINE DERIVATIVES

[75] Inventors: Michael R. Cohen, West Orange; Richard W. Kierstead; Jefferson W. Tilley, both of North Caldwell, all of N.J.

[73] Assignee: Hoffmann-La Roche Inc., Nutley, N.J.

[21] Appl. No.: 883,779

[22] Filed: Mar. 6, 1978

Related U.S. Application Data

[62] Division of Ser. No. 763,172, Jan. 27, 1977, Pat. No. 4,096,276, which is a division of Ser. No. 677,106, Apr. 15, 1976, abandoned.

[51] Int. Cl.$^2$ ................... A61K 31/445; A61K 31/17; A61K 31/155
[52] U.S. Cl. ................................... 424/267; 424/322; 424/326; 424/330
[58] Field of Search ............... 424/326, 322, 330, 267

[56] References Cited

PUBLICATIONS

Spivakova—Chem. Abst., vol. 76 (1972), p. 108.

Primary Examiner—Sam Rosen
Attorney, Agent, or Firm—Jon S. Saxe; George M. Gould; William G. Isgro

[57] ABSTRACT

Antihypertensively active thiourea derivatives of the formulas

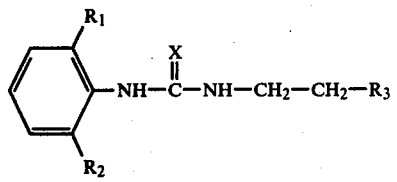

I and

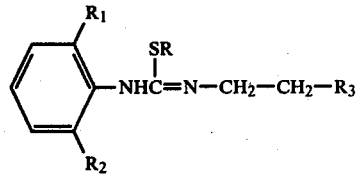

II wherein R, $R_1$, $R_2$, $R_3$ and X are as hereinafter described, as well as a method of using a compound of the formula

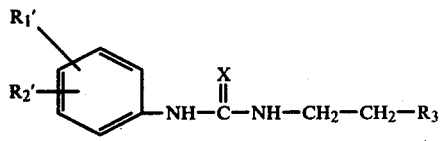

III wherein $R_1'$, $R_2'$, $R_3$ and X are as previously described, or a compound of formula II as an anti-hypertensive agent, is described.

4 Claims, No Drawings

METHOD OF REDUCING BLOOD PRESSURE WITH THIOUREA DERIVATIVES AND GUANIDINE DERIVATIVES

This is a division of application Ser. No. 763,172, filed Jan. 27, 1977 now U.S. Pat. No. 4,096,276, which in turn is a division of application Ser. No. 677,106, filed Apr. 15, 1976, now abandoned.

BRIEF SUMMARY OF THE INVENTION

Thiourea derivatives of the formulas

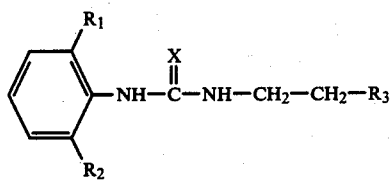

and

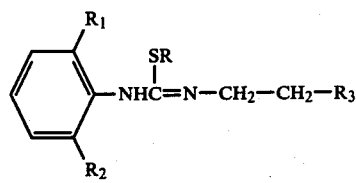

wherein R is lower alkyl; $R_1$ and $R_2$, independently, are halogen; $R_3$ is amino or piperidino; and X is sulfur or imino; and addition salts thereof with pharmaceutically acceptable acids, are described. The compounds of formulas I and II are useful as anti-hypertensive agents.

In another aspect, the invention relates to a method of treating hypertension which comprises administering to a host requiring such treatment an effective amount of a compound of the formula

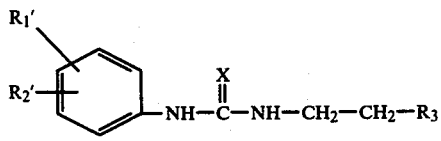

wherein $R_1'$ and $R_2'$, independently, are hydrogen, halogen or lower alkyl; X is sulfur or imino; and $R_3$ is amino or piperidino, or a compound of formula II, or an addition salt thereof with a pharmaceutically acceptable acid.

DETAILED DESCRIPTION OF THE INVENTION

As used herein, the term "lower alkyl" denotes a straight or branched chain hydrocarbon of 1–7 carbon atoms, such as methyl, ethyl, propyl, butyl, isobutyl, pentyl, heptyl, and the like. The term "halogen" denotes fluorine, bromine and chlorine; chlorine is preferred. The term "lower alkanoyl" denotes a radical derived from an aliphatic carboxylic acid of 1 to 7 carbon atoms, for example, formyl, acetyl, propionyl, and the like.

The invention comprises compounds of the formulas

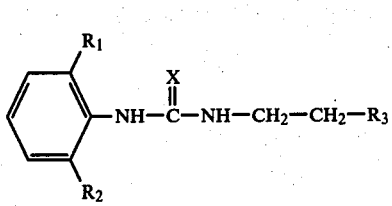

and

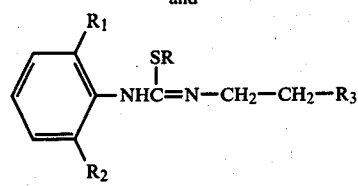

wherein R is lower alkyl; $R_1$ and $R_2$, independently, are halogen; $R_3$ is amino or piperidino; and X is sulfur or imino; and addition salts thereof with pharmaceutically acceptable acids.

Exemplary of the compounds of formulas I and II of the invention are:
1-(2-aminoethyl)-3-(2,6-dichlorophenyl)-thiourea;
1-(2-aminoethyl)-3-(2,6-dibromophenyl)-thiourea;
1-(2-aminoethyl)-3-(2,6-difluorophenyl)-thiourea;
1-(2-aminoethyl)-3-(2,6-dichlorophenyl)-2-methylthiopseudourea dihydrochloride;
1-(2,6-dichlorophenyl)-3-[2-(1-piperidino)ethyl]-2-thiourea;
1-(2-aminoethyl)-3-(2,6-dichlorophenyl)-guanidine;
and the like.

The most preferred compound of the invention is 1-(2-aminoethyl)-3-(2,6-dichlorophenyl)-thiourea.

The compounds of the invention can be prepared as hereinafter described.

A compound of formula I wherein X is sulfur, can be prepared by treating the corresponding compound of the formula

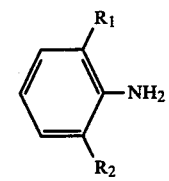

wherein $R_1$ and $R_2$ are as previously described, which is a known compound, with ammonium thiocyanate and benzoyl chloride, in an inert organic solvent, for example, acetone, a chlorinated hydrocarbon such as chloroform, methylene chloride or the like, preferably at the reflux temperature of the reaction mixture. The reaction product is treated with an alkali metal hydroxide, such as sodium hydroxide, to obtain a compound of the formula

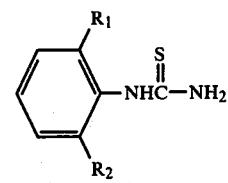

wherein $R_1$ and $R_2$ are as previously described.

Thereafter, a compound of formula V is converted to a compound of the formula

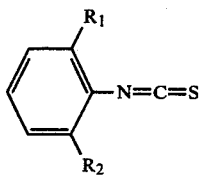

wherein $R_1$ and $R_2$ are as previously described, according to known procedures, for example, by heating a compound of formula V at the reflux temperature of the reaction mixture in the presence of a solvent, for example, a halobenzene, such as chlorobenzene. Upon evaporation of the solvent and crystallization or distillation of the residue, a compound of formula VI is obtained.

Advantageously, a compound of formula IV can also be converted to a compound of formula VI directly by treatment with thiophosgene in a solvent, for example, a halobenzene such as chlorobenzene or the like, containing dimethylformamide, at the reflux temperature of the reaction mixture. Upon evaporation of the solvent and distillation of the residue, the desired compound of formula VI is obtained.

A compound of formula VI is converted to a compound of the formula

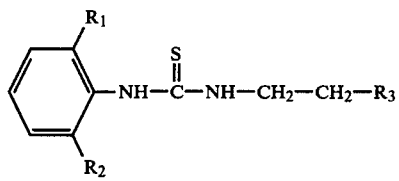

wherein $R_1$, $R_2$ and $R_3$ are as previously described, by treating a compound of formula VI with ethylenediamine or aminoethylpiperidine in an inert organic solvent, for example, benzene, tetrahydrofuran, an alkanol such as ethanol or the like, methylene chloride or the like, at room temperature or at the reflux temperature of the reaction mixture. The reaction product of formula Ia can be recovered either by crystallization or by suitable extraction, for example, with a halogenated hydrocarbon such as methylene chloride.

A compound of the formula

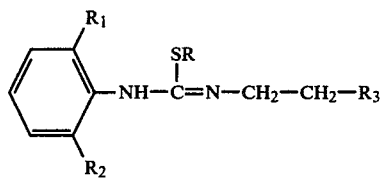

wherein R, $R_1$, $R_2$ and $R_3$ are as previously described, can be obtained by treating a compound of formula Ia with an alkyl halide such as iodomethane in the presence of an inorganic acid, for example, a hydrohalic acid, such as hydrochloric acid, in an organic solvent, for example, an alkanol such as methanol. Conveniently, the reaction is carried out at the refluxing temperature of the reaction mixture. The desired compound of formula II is recovered by basification of the reaction mixture, for example, with an alkali metal hydroxide such as sodium hydroxide or the like, and extraction with a solvent, for example, a halogenated hydrocarbon such as methylene chloride or the like.

A compound of formula I wherein X is imino, can be prepared by treating the corresponding compound of the formula

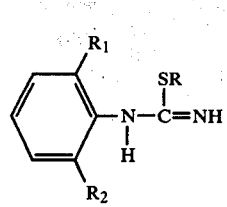

wherein R, $R_1$ and $R_2$ are as previously described, with a lower alkanoyl ethylenediamine in an inert organic solvent, for example, an alkanol such as amyl alcohol, at a temperature in the range of from about 150° to about 200° C., to obtain a compound of the formula

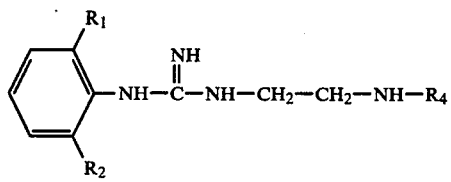

wherein $R_1$ and $R_2$ are as previously described, and $R_4$ is alkanoyl.

The resulting compound of formula VIII can be separated, upon cooling of the reaction mixture, by partitioning the reaction mixture between an aqueous alkali metal hydroxide such as sodium hydroxide, and a halogenated hydrocarbon solvent such as methylene chloride, and recovering the desired compound from the halogenated hydrocarbon solvent.

A compound of formula VIII is deacylated by known procedures, for instance, by treatment with an inorganic acid, for example, a hydrohalic acid such as hydrochloric acid or the like, at the reflux temperature of the reaction mixture to obtain a compound of the formula

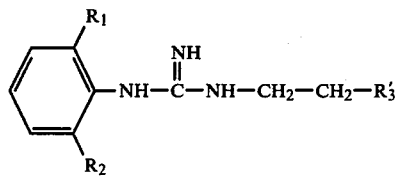

wherein $R_1$ and $R_2$ are as previously described, and $R_3'$ is amino.

The desired compound of formula Ib can be recovered by evaporation and, if required, crystallization.

The compounds of formulas I and II above are basic compounds which form acid addition salts with inorganic or organic acids. Thus, they form pharmaceutically acceptable acid addition salts with both pharmaceutically acceptable organic and inorganic acids, such as, hydrohalides, e.g., hydrochloride, hydrobromide, other mineral acid salts, such as, sulfate, nitrate, phosphate and the like, alkyl and mono-aryl sulfonates, such as, ethanesulfonate, toluenesulfonate, benzenesulfonate, or the like, other organic acids such as formate, tartrate, maleate, citrate, benzoate, salicylate, ascorbate, or the like. Non-pharmaceutically acceptable acid addition salts of compounds of formulas I and II above can be converted into pharmaceutically acceptable acid addition salts via conventional metathetic reactions whereby the non-pharmaceutically acceptable anion is replaced by a pharmaceutically acceptable anion; or alternatively, by neutralizing the nonpharmaceutically acceptable acid addition salt and then reacting the so-obtained free base with a reagent yielding a pharmaceutically acceptable anion.

The present invention also relates to a method of reducing blood pressure by administering to a host, i.e., a warm-blooded animal requiring such treatment, an effective amount of a compound of the formula

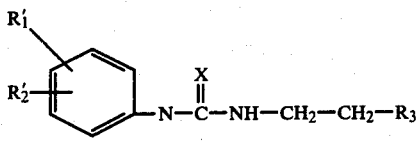

wherein $R_1'$ and $R_2'$, independently, are hydrogen, halogen or lower alkyl; X is sulfur or imino; and $R_3$ is amino or piperidino, or an addition salt thereof with a pharmaceutically acceptable acid, or a compound of the formula

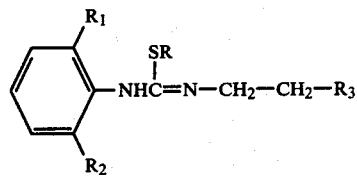

wherein R is lower alkyl; $R_1$ and $R_2$, independently, are halogen; and $R_3$ is amino or piperidino or an addition salt thereof with a pharmaceutically acceptable acid. The compounds of formula III, which are inclusive of the compounds of formula I, form acid addition salts with inorganic or organic acids, as described above, for the compounds of formulas I and II.

Exemplary of the compounds of formula III, other than the encompassed compounds of formula I, are 1-(2-aminoethyl)-3-(2,3-dichlorophenyl)-thiourea, 1-(2-aminoethyl)-3-(2-methyl-4-chlorophenyl)-thiourea, and the like.

The compounds of formula II and formula III, which includes the compounds of formula I, and salts thereof, possess hypotensive activity, that is, reduce the blood pressure in warm-blooded animals, and are therefore useful as antihypertensive agents in warm-blooded animals.

The anti-hypertensive activity of the compounds of the invention of formulas I and II, as well as those of formula III, which is inclusive of the compounds of formula I, can be demonstrated in either genetically or deoxycorticosterone acetate/sodium chloride fed hypertensive rats 12-15 weeks of age. For example, Doca-Na hypertension is induced in Charles River male rats weighing 170-210 grams by unilateral nephrectomy followed by subcutaneous implantation of a 25 mg. deoxycorticosterone acetate pellet. Animals are placed in individual cages and receive 0.9% sodium chloride solution and rat chow diet ad libitum. Two weeks are allowed to elapse from the time of surgery for development of hypertension, i.e., systolic blood pressure above 150 mm Hg. Systolic blood pressure is measured indirectly from the tail of unanesthetized rats (restrained in holders heated for 5-10 minutes at 37°-38° C.) using a pneumatic pulse transducer (piezo-electric crystal and occluding cuff). The transducer and occluding cuff are coupled to a two-channel recorder. Control readings are taken prior to drug and at 1, 3, 6 and 24 hours post-drug. All test compounds are prepared in acacia solution (5%) and are orally administered to the test animals.

When 1-(2-aminoethyl)-3-(2,6-dichlorophenyl)thiourea, which has demonstrated an $LD_{50}$ of 750-775 mg/kg p.o. and $LD_{50}$ of 450-550 mg/kg i.p. in the mouse, is utilized in the above test procedure at a dose of 10 mg/kg p.o., a decrease in the blood pressure of 73 mm/Hg and a decrease of 81 beats/minutes in the heart rate 6 hours after administration of the test substance are observed.

When 1-(2-aminoethyl)-3-(2,3-dichlorophenyl)thiourea, which has demonstrated an $LD_{50}$ of $>1000$ mg/kg p.o. and $LD_{50}$ of 450 mg/kg i.p. in the mouse, is utilized the above test procedure at a dose of 10 mg/kg p.o., a decrease in the blood pressure of 51 mm/Hg and a decrease of 95 beats/minutes in the heart rate 6 hours after administration of the test substance are observed.

The compounds of formulas I and II as well as the compounds of formula III, which is inclusive of the compounds of formula I, or salts thereof as herein described, can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkylene-glycols, and the like. The pharmaceutical preparations can be employed in a solid form, for example, as tablets, troches, suppositories, capsules, or in liquid form, for example, as solutions, suspensions, or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

A suitable pharmaceutical dosage unit contains from about 0.1 to 5 mg. of a compound of formula I and II, as well as a compound of formula III, or an equivalent amount of a pharmaceutically acceptable acid addition salt thereof. Suitable oral dosage regimens in warm-blooded mammals comprise from about 0.1 mg/kg. per day to about 5 mg/kg. per day. Suitable parenteral dosage regimens in warm-blooded mammals comprise from about 0.05 mg/kg. per day to about 2.5 mg/kg. per day. However, for any particular subject, the specific dosage regimen should be adjusted according to individual need and the professional judgment of the person administering or supervising the administration of a compound of formula I or II, as well as a compound of formula III. It is to be understood that the dosages set forth herein are exemplary only and that they do not, to any extent, limit the scope or practice of this invention.

The compounds of formulas I and II, as well as the compounds of formula III, and their pharmaceutically acceptable acid addition salts, have effects qualitatively similar to those of catapress, known for its therapeutic uses and properties. Thus, the compounds of this invention demonstrate a pattern of activity associated with antihypertensive agents of known efficacy and safety.

The compounds of formulas I and II have central nervous system activity, including antidepressant activity. The antidepressant activity can be demonstrated in warm-blooded animals. For example, six mice are treated with the test compound. One hour later a ptosis-inducing dose of tetrabenazine (normally 150 mg/kg) is given intraperitoneally. Ptosis is read one hour after the tetrabenazine injection. The $ED_{50}$ is the dose at which ptosis is prevented in 3/6 of the mice. The numbers of mice exhibiting ptosis are counted. The $ED_{50}$ is calculated by the method of Behrens. Arch. Exp. Path. & Pharm. 140, 237 (1929).

When 1-(2-aminoethyl)-3-(2,6-dichlorophenyl)-thiourea is utilized as the test compound in the above procedure, it demonstrates an $ED_{50}$ of 5.7 mg/kg.

The following Examples further illustrate the invention. All temperatures are in degrees Centigrade, unless otherwise stated.

EXAMPLE 1

Preparation of 1-(2-aminoethyl)-3-(2,6-dichlorophenyl)thiourea

To an ice cold solution of 350 ml. of ethylenediamine in 150 ml. of tetrahydrofuran was added a solution of 50.0 g. of 2,6-dichlorophenylisothiocyanate in 150 ml. of tetrahydrofuran over a period of 4 hours. The resulting solution was stirred overnight at room temperature and concentrated. The product was partitioned between 1 l. of 1N hydrochloric acid and 600 ml. of methylene chloride. The aqueous layer was extracted at 2×300 ml. of methylene chloride, made basic with 4N sodium hydroxide, and extracted 3×500 ml. of methylene chloride. The combined base extracts were washed 1×100 ml. of water, dried over potassium carbonate and concentrated to give 53.8 g. (83%) of 1-(2-aminoethyl)-3-(2,6-dichlorophenyl)thiourea, m.p. 136°–138°. Recrystallization from ethyl acetate gave the analytical sample, m.p. 135°–137°.

EXAMPLE 2

Preparation of 1-(2,6-dichlorophenyl)thiourea

A dry 500 ml. flask was charged with a solution of 17 g. of ammonium thiocyanate in 100 ml. of acetone, and 23.3 ml. of benzoyl chloride was added over a period of 5 minutes. On completion of the addition, the mixture was refluxed for 5 minutes, and upon cooling, a solution of 320 g. of 2,6-dichloroaniline in 100 ml. of acetone was added over a 10-minute period. After stirring for 10 minutes, the reaction mixture was poured onto 1.5 l. of water, and the yellow precipitate was collected. This material was suspended in 300 ml. of 10% sodium hydroxide, which was heated to reflux for 15 minutes and filtered hot to give 369.2 g. (85%) of 1-(2,6-dichlorophenyl)thiourea, m.p. 158°–160°.

EXAMPLE 3

Preparation of 2,6-dichlorophenylisothiocyanate

A solution of 156.9 g. of 1-(2,6-dichlorophenyl)thiourea in 1 l. of chlorobenzene was refluxed for 20 hours and concentrated. The resulting oil was triturated with 1 l. of hot hexane which was filtered. On cooling overnight, 52 g. (36%) of 2,6-dichlorophenylisothiocyanate, m.p. 41°–42° separated. Concentration of the filtrate gave an additional 64.2 g. (44%), m.p. 41°–43° in two crops. Recrystallization of a sample from hexane gave the analytical sample, m.p. 41°–42°.

This substance can also be prepared as follows:

A solution of 800 g. of 2,6-dichloroaniline in 3.2 l. of chlorobenzene, 69 ml. of dimethylformamide and 708 ml. of thiophosgene was heated slowly as the reaction mixture foamed, to 110°. After 30 minutes at 110°, the mixture was cooled to 70°, filtered through a pad of silica gel and concentrated to dryness. The resulting oil was distilled to give 947 g. (94%) of 2,6-dichlorophenylisothiocyanate, bp 100°/0.3 mm, m.p. 41°–42°.

EXAMPLE 4

Preparation of 1-(2-aminoethyl)-3-(2,6-dichlorophenyl)-2-methylthiopseudourea dihydrochloride A solution of 12.68 g. of 1-(2-aminoethyl)-3-(2,6-dichlorophenyl)thiourea in 80 ml. of ethanol, 4.0 ml. of concentrated hydrochloric acid and 12 ml. of iodomethane was refluxed for 2 hours. On cooling, the mixture was poured onto 200 ml. of water and sufficient 4N sodium hydroxide was added to bring the pH to 11. The aqueous solution was extracted 3×150 ml. of methylene chloride, and the combined organic layers were washed 1×100 ml. of water, dried over potassium carbonate and concentrated. The resulting gum gave a solid on standing, i.e., 1-(2-aminoethyl)-3-(2,6-dichlorophenyl)-2-methylthiopseudourea, m.p. 74°–79°, whose spectral data were consistent with the assigned structure. The material was too labile for purification and was acidified with hydrochloric acid and crystallized from ethanol-ether to give 14.10 g. (84%) of 1-(2-aminoethyl)-3-(2,6-dichlorophenyl)-2-methylthiopseudourea dihydrochloride, m.p. 179°–184°. Two crystallizations from ethanol-ether gave an analytical sample, m.p. 179°–182°.

EXAMPLE 5

Preparation of 1-(2-aminoethyl)-3-(2,6-dibromophenyl)thiourea

In a similar manner to that described in Example 1, ethylenediamine was reacted with 2,6-dibromophenylisothiocyanate to yield 1-(2-aminoethyl)-3-(2,6-dibromophenyl)thiourea, melting point 155°–157°.

EXAMPLE 6

Preparation of 1-(2,6-dibromophenyl)thiourea

A solution of 4.6 ml. of benzoyl chloride in 10 ml. of acetone was added over a period of 5 minutes to a solution of 3.32 g. of ammonium thiocyanate in 60 ml. of dry acetone at reflux. The resulting solution was refluxed for 10 minutes and a solution of 10.0 g. of 2,6-dibromoaniline in 40 ml. of acetone was added over a period of 10 minutes. After 15 minutes at reflux, the reaction mixture was poured onto 300 ml. of water and filtered. The resulting solid was suspended in 30 ml. of 10% sodium hydroxide and boiled for 10 minutes. The clear solution was acidified, neutralized to pH 8 with ammonia and filtered, giving 12.0 g. (97%) of 1-(2,6-dibromophenyl)thiourea, m.p. 186°–189°. Recrystallization from aqueous methanol gave the analytical sample, m.p. 192°–193°.

EXAMPLE 7

Preparation of 2,6-dibromophenylisothiocyanate

A suspension of 101 g. (0.326 mole) of 1-(2,6-dibromophenyl)thiourea in 1 l. of chlorobenzene was stirred and refluxed 20 hours, and the resulting solution was filtered and evaporated. The tan solid obtained was triturated with boiling petroleum ether and filtered. On cooling, the filtrate deposited 63.4 g. of yellow needles of 2,6-dibromophenylisothiocyanate, m.p. 63°–65°. A portion was recrystallized from ether-petroleum ether to give the analytical sample, m.p. 65°–66°.

EXAMPLE 8

Preparation of 1-(2-aminoethyl)-3-(2,6-difluorophenyl)thiourea

A solution of 11.1 g. of 2,6-difluorophenylisothiocyanate in 30 ml. of tetrahydrofuran was added to an ice cold solution of 100 ml. of ethylene diamine in 100 ml. of tetrahydrofuran over the course of 10 minutes. The reaction mixture was stirred overnight at room temperature, concentrated in vacuo, and partitioned between 50 ml. of methylene chloride and 200 ml. of water. The aqueous layer was extracted 2×50 ml. methylene chloride and the combined organic layers were dried over potassium carbonate and evaporated to a foam which on trituration with ethanol-water gave 1.06 g. (8%) of 1,1-ethylenebis-[3-(2,6-difluorophenyl)-2-thiourea]. Two recrystallizations from ethanol-water gave an analytical sample, m.p. 200°-204°.

The aqueous layer from above was evaporated to 14.8 g. of a brown oil which was dissolved in water and passed through a column of 300 ml. of Dowex-50-W cation exchange resin in the H+ form. Elution with 500 ml. portions of water, 20% aqueous pyridine, and 20% aqueous triethylamine gave only traces of unidentified material. Further elution with 800 ml. of 1:1:3 triethylamine-ethanol-water gave an oil which was acidified with succinic acid and crystallized from ethanol-ether to give 9.83 g. of the succinate salt of 1-(2-aminoethyl)-3-(2,6-difluorophenyl)thiourea, m.p. 74°-79°. The filtrate gave an additional 0.93 g., m.p. 68°-75°. Recrystallization from ethanol-ether gave the analytical sample, m.p. 80°-84°.

EXAMPLE 9

Preparation of 2,6-difluorophenylisothiocyanate

A suspension of 11.0 g. of 2,6-difluoroaniline in 100 ml. of 1N hydrochloric acid and 50 ml. of methylene chloride was stirred mechanically as 6.8 ml. of thiophosgene was added. After remaining for three hours at room temperature, the layers were separated, and the aqueous phase was extracted 2×100 ml. of methylene chloride. The combined organic layers were washed 1×50 ml. of water, dried over magnesium sulfate and evaporated. The resulting oil was distilled, and the fraction boiling 160°-165°, 100 mm was collected, and yielded 11.1 g. (78%) of 2,6-difluorophenylisothiocyanate.

EXAMPLE 10

Preparation of 1-(2-aminoethyl)-2-(2,6-dichlorophenyl)guanidine dihydrochloride

A solution of 16.57 g. of 1-(2-acetylaminoethyl)-2-(2,6-dichlorophenyl)guanidine in 150 ml. of concentrated hydrochloric acid was refluxed for 16 hours and was concentrated under reduced pressure. Trituration with ethanol gave 24.06 g. of a white solid which was recrystallized from aqueous ethanol-ether to give 14.18 g. (77%) of 1-(2-aminoethyl)-2-(2,6-dichlorophenyl)-guanidine dihydrochloride, m.p. 154°-160° partly melt, 222°-224° clear. On addition of ether, the filtrate gave an additional 4.81 g. (26%) m.p. 155°-160° partly melt, 221°-224° clear.

EXAMPLE 11

Preparation of 1-(2-acetylaminoethyl)-2-(2,6-dichlorophenyl)guanidine

A solution of 45.0 g. of 1-(2,6-dichlorophenyl)-2-methylthiopseudourea and 44.75 g. of N-acetylethylenediamine in 35 ml. of amyl alcohol was heated at a bath temperature of 180° for 3 hours. On cooling, the mixture was partitioned between 250 ml. portions of 1 N sodium hydroxide and methylene chloride. The aqueous layer was extracted 2×250 ml. of methylene chloride and the combined organic layers were washed with 1×200 ml. water, dried ($K_2CO_3$), and evaporated to an oil. Trituration with ether gave 16.56 g. (46%) of 1-(2-acetylaminoethyl)-2-(2,6-dichlorophenyl)guanidine, m.p. 186°-193°.

Further addition of ether to the filtrate gave an additional 1.01 g. (3%), m.p. 184°-193°. Two crystallizations from methylene chloride-hexane gave the analytical sample m.p. 196°-198°.

EXAMPLE 12

Preparation of 1-(2,6-dichlorophenyl)-3-[2-(1-piperidino)ethyl]-2-thiourea

In a similar manner to that described in Example 1, 1-(2-aminoethyl)piperidine was reacted with 2,6-dichlorophenyl-isothiocyanate to yield directly (without extraction) 1-(2,6-dichlorophenyl)-3-[2-(1-piperidino)ethyl]-2-thiourea, melting point 165°-168°. The hydrochloride salt melts at 205°-208°.

EXAMPLE 13

| Tablet Formulation | |
|---|---|
| Ingredient | mg/tablet |
| 1-(2-aminoethyl)-3-(2,6 dichlorophenyl)-thiourea | 1.00 |
| Lactose Anhydrous | 137.00 |
| Microcrystalline Cellulose | 40.00 |
| Cornstarch | 20.00 |
| Magnesium Stearate | 2.00 |
| Weight of Tablet | 200.00 mg. |

Procedure:

A premix of 1 part of 1-(2-aminoethyl)-3-(2,6-dichlorophenyl)-thiourea and part of 137 parts of anhydrous lactose is prepared and milled. The remaining lactose is added to the premix, as well as 40 parts of microcrystalline cellulose and 20 parts of cornstarch, and milled for 15 minutes. To this is added 2 parts of magnesium stearate with mixing for 2 minutes. Tablets are prepared by compression on a suitable punch.

EXAMPLE 14

| Tablet Formulation | |
|---|---|
| Ingredients | mg/tablet |
| 1-(2-aminoethyl)-3-(2,6 dichlorophenyl)-thiourea | 1.00 |
| Lactose Hydrous | 162.00 |
| Modified Starch | 15.00 |
| Pregelatinized Starch | 20.00 |
| Magnesium Stearate | 2.00 |
| Weight of Tablet | 200.00 |

Procedure:

A premix of one part of 1-(2-aminoethyl)-3-(2,6-dichlorophenyl)-thiourea and part of 162 parts of hydrous lactose is prepared and milled. The resulting mixture is mixed with the remainder of the hydrous lactose, 15 parts of modified starch and 20 parts of pregelatinized starch and granulated with water. The resulting granulation is dried overnight, milled and mixed with 2 parts of magnesium stearate. Tablets are prepared by compression on a suitable punch.

EXAMPLE 15

| Capsule Formulation | |
|---|---|
| 1-(2-aminoethyl)-3-(2,6 dichlorophenyl)-thiourea | 1.00 |
| Lactose Hydrous | 163.00 |
| Cornstarch | 30.00 |
| Talc | 5.00 |
| Magnesium Stearate | 1.00 |
| Weight of Capsule | 200.00 |

Procedure:

A premix of one part of 1-(2-aminoethyl)-3-(2,6-dichlorophenyl)-thiourea and part of 163 parts of hydrous lactose is prepared and milled. Thereafter, the remaining lactose and 30 parts of cornstarch are added to the milled mixture and mixed well. Subsequently, 5 parts of talc and 1 part of magnesium stearate are added and the entire batch is mixed for 5 minutes and encapsulated in hardshell capsules.

We claim:

1. A method of reducing blood pressure which comprises administering to a host requiring such treatment an effective amount of a compound of the formula

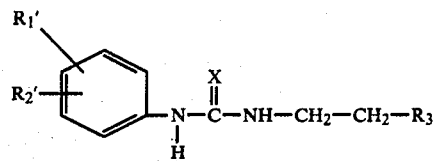

wherein $R_1'$ and $R_2'$, independently, are hydrogen, halogen or lower alkyl; X is sulfur or imino; and $R_3$ is amino or piperidino, provided that when X is sulfur, $R_3$ is other than amino, or a compound of the formula

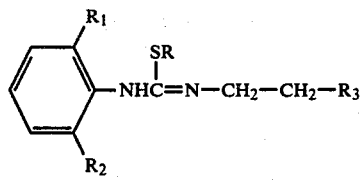

wherein R is lower alkyl; $R_1$ and $R_2$, independently, are halogen; and $R_3$ is amino or piperidino, or an addition salt thereof with a pharmaceutically acceptable acid.

2. In accordance with claim 1, a method of reducing blood pressure which comprises administering to a host requiring such treatment an effective amount of 1(2,6-dichlorophenyl)-3-[2-(1-piperidino)-ethyl]-2-thiourea.

3. In accordance with claim 1, a method of reducing blood pressure which comprises administering to a host requiring such treatment an effective amount of 1-(2-aminoethyl)-3-(2,6-dichlorophenyl)-guanidine.

4. In accordance with claim 1, a method of reducing blood pressure which comprises administering to a host requiring such treatment an effective amount of 1-(2-aminoethyl)-3-(2,6-dichlorophenyl)-2-methylthiopseudourea.

* * * * *